United States Patent [19]
Dorta et al.

[11] Patent Number: 5,929,265
[45] Date of Patent: Jul. 27, 1999

[54] BINUCLEAR IRIDIUM(I) PHOSPHINE COMPLEXES AND THEIR USE AS CATALYST IN THE ASYMMETRIC HYDROAMINATION OF OLEFINS

[75] Inventors: Romano Dorta, Chur; Patrick Egli, Alpnach; Nikolaus H Bieler, Glis; Antonio Togni, Oberwil; Martin Eyer, Glis, all of Switzerland

[73] Assignee: Lonza AG, Gampel/Valais

[21] Appl. No.: 09/170,114

[22] Filed: Oct. 13, 1998

[30] Foreign Application Priority Data

Oct. 14, 1997 [CH] Switzerland ............... 2392/97

[51] Int. Cl.$^6$ ............... C07F 9/28; C07F 15/00; C07D 209/04; C07C 209/00
[52] U.S. Cl. ............... 556/14; 556/18; 556/21; 556/136; 564/414; 564/488; 548/490; 548/508
[58] Field of Search ............... 556/18, 21, 14, 556/136; 564/414, 488; 548/490, 508

[56] References Cited

U.S. PATENT DOCUMENTS

| | | | |
|---|---|---|---|
| 4,215,066 | 7/1980 | Kalck et al. | 260/429 R |
| 5,112,999 | 5/1992 | Osborn et al. | 556/23 |

FOREIGN PATENT DOCUMENTS

| | | |
|---|---|---|
| 0564406 | 3/1993 | European Pat. Off. |
| 0612758 | 2/1994 | European Pat. Off. |

OTHER PUBLICATIONS

A. Togni et al., Inorg. Chem. Acta (1994), 222, 213–224.
Y. Hayashi et al., J. Organomet. Chem., (1995), 503, 143–148.

*Primary Examiner*—Porfirio Nazario-Gonzalez
*Attorney, Agent, or Firm*—Fisher, Christen & Sabol

[57] ABSTRACT

Binuclear iridium (I) phosphine complexes of the general formula:

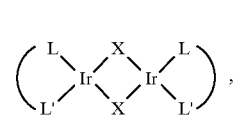

in which X is fluorine, chlorine, bromine or iodine, and

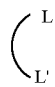

is in each case a chiral bidentate diphosphine ligand. The complexes are particularly suitable as catalysts for the inter- or intramolecular asymmetric hydroamination of prochiral olefins.

38 Claims, No Drawings

BINUCLEAR IRIDIUM(I) PHOSPHINE COMPLEXES AND THEIR USE AS CATALYST IN THE ASYMMETRIC HYDROAMINATION OF OLEFINS

BACKGROUND OF THE INVENTION

1. Field of the Invention

The invention relates to neutral binuclear iridium (I) phosphine complexes of the general formula:

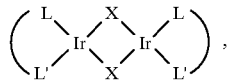

in which X is fluorine, chlorine, bromine or iodine, and

is in each case a chiral bidentate diphosphine ligand. The complexes have a quadratic-planar configuration at the iridium centers and can thus occur in two stereoisomeric forms (cis- and trans-form) if the diphosphine ligands do not have a $C_2$ symmetry relationship between the two phosphorus atoms. In these cases, here and in the text below both stereoisomers are always intended, both in the pure form and also as a mixture.

The invention also relates to a process for the preparation of those complexes.

Furthermore, the invention relates to processes for the asymmetric hydroamination of olefins under catalysis by iridium (I) phosphine complexes of the formula I.

2. Background of the Invention

The asymmetric hydroamination of olefins is a potentially important method for preparing optically active amines. To date, however, only a few practical examples of this reaction are known; in particular, there is a lack of satisfactory processes for intermolecular hydroamination. The examples known to date are notable in particular for low activity of the catalysts used and correspondingly low reaction rates. In addition, the catalyst often only survives a few catalytic cycles, which renders the process unusable for industrial application.

BROAD DESCRIPTION OF THE INVENTION

The object of the invention is to provide catalysts which, in asymmetric hydroamination, have a higher activity over a large number of catalytic cycles and give high optical yields.

According to the invention, this object is achieved by the binuclear iridium (I) phosphine complexes of the invention.

Other objects and advantages of the invention are set out herein or are obvious herefrom to one skilled in the art. These objects and advantages are achieved by the complexes and processes of the invention.

It has been found that complexes of the general formula:

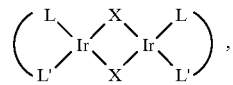

in which X is fluorine, chlorine, bromine or iodine, and

is in each case a chiral bidentate diphosphine ligand, can be readily prepared by a suitable process.

Chiral bidentate diphosphine ligands are molecules which have at least one chiral element (chiral center, chiral plane or chiral axis) and two coordinatable tertiary phosphorus atoms of oxidation number −3, the spatial arrangement of the phosphorus atoms permitting the formation of a chelate ring. Numerous ligands of this type having a variety of basic structures are known from the literature, in particular those which have a biaryl system, such as, biphenyl or 1,1'-binaphthalene or a metallocene system as basic structure. Some of the ligands which can be used according to the invention are available commercially, and others can be prepared by known processes or by analogy with such (see, e.g.: A. Togni et al., *Inorg. Chim. Acta*, 1994, 222, 213–224; Y. Hayashi et al., *J. Organomet. Chem.*, 1995, 503, 143–148; European Published Patent Application No. 0564406; and European Published Patent Application No. 0612758).

The complexes according to the invention are preferably isolated in solid form.

The chiral bidentate diphosphine ligands are preferably 1,2-disubstituted ferrocenes with the phosphino groups on the two substituents. These ferrocenes preferably have the general formula:

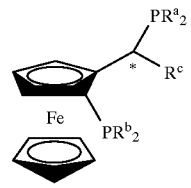

in which the radicals $R^a$ and $R^b$ are identical or different and are each $C_{1-6}$-alkyl, optionally substituted phenyl or $C_{3-8}$-cycloalkyl, or the two radicals $R^a$ and/or $R^b$, together with the adjacent phosphorus atom, form a monocyclic or bicyclic system having from 3 to 9 ring members. Particularly preferred meanings of $R^a$ and $R^b$ are tert-butyl, phenyl, 3,5-dimethylphenyl, 4-tert-butyl-phenyl and cyclohexyl. Particular preference is likewise given to compounds in which the two radicals $R^a$ and/or $R^b$, together with the adjacent phosphorus atom, form a 9-phosphabicyclo[3.3.1] nonane.

$R^c$ is $C_{1-6}$-alkyl, preferably methyl. The asterisk (*) indicates a chiral center. The 1,2-disubstituted ferrocenes are known compounds or are obtainable in the same way as known compounds by known methods. (See e.g.: European Published Patent Application No. 0612758; European Published Patent Application No. 0564406; and A. Togni et al., *Inorg. Chim. Acta*, 1994, 222,213–224.)

The chiral bidentate diphosphine ligands are preferably chosen from the group consisting of (R)-2,2'-bis (diphenylphosphino)-1,1'-binaphthalene, (S)-2,2'-bis (diphenylphosphino)-1,1'-binaphthalene, (R)-2,2'-bis (diphenylphosphino)-6,6'-dimethyl-1,1'-biphenyl, (S)-2,2'-bis(diphenylphosphino)-6,6'-dimethyl-1,1'-biphenyl, 1-[1 (R)-(dicyclohexylphosphino)ethyl]-2(S)-(diphenylphosphino)ferrocene, 1-[1(S)-(dicyclohexylphosphino)ethyl]-2(R)-(diphenylphosphino) ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino) ferrocene, 1-[1(R)-(diphenylphosphino)ethyl]-2(S)-(di-tert-butylphosphino)ferrocene, 1-[1(S)-(diphenylphosphino) ethyl]-2(R)-(di-tert-butylphosphino)ferrocene, 1-{1(R)-[bis (3,5-dimethylphenyl)phosphino]ethyl}-2(S)-(diphenylphosphino)ferrocene, 1-{1(S)-[bis(3,5-dimethylphenyl)phosphino]ethyl}-2(R)-(diphenylphosphino)-ferrocene, 1-{1(R)-[bis(4-tert-butylphenyl)phosphino]-ethyl}-2(S)-(diphenylphosphino) ferrocene, 1-{1(S)-[bis(4-tert-butylphenyl)phosphino] ethyl}-2(R)-(diphenylphosphino)ferrocene, 1-[1(S)-(9-phosphabicyclo[3.3.1]nonan-9-yl)ethyl]-2(R)-(diphenylphosphino)ferrocene and 1-[1(R)-(9-phosphabicyclo[3.3.1]nonan-9-yl)ethyl]-2(S)-(diphenylphosphino)ferrocene. Particular preference is given to those complexes according to the invention in which X is chlorine.

The complexes according to the invention can be prepared, for example, by reacting a suitable iridium (I) olefin complex, such as, [IrX(coe)$_2$]$_2$ (coe=cyclooctene) or [IrX(C$_2$H$_4$)$_4$], in which X is in each case the halogen which acts as a bridging ligand in the bidentate complex, with the corresponding chiral bidentate diphosphine ligand in a ligand exchange reaction in a nonpolar solvent. The nonpolar solvent is preferably benzene or toluene.

The complexes according to the invention can be isolated and purified by methods known per se, for example, by evaporating the reaction mixture, the olefins liberated during ligand exchange evaporating with the solvent, and optionally recrystallizing the residue. Separation of the cis-/trans-isomeric mixtures obtained from diphosphine ligands with non-equivalent phosphorus atoms is not, however, usually possible in this way. Depending on their solubility, the complexes can also be recrystallized directly from the reaction mixture.

The complexes according to the invention are preferably used as catalysts or catalyst precursors in the asymmetric hydroamination of prochiral olefins. The term "catalyst precursor" in this connection means that the actual catalytically active species, if present, only forms under the reaction conditions of the hydroamination. In this connection, prochiral olefins are taken to mean those which produce chiral products when an asymmetric compound A–B is formally added to the double bond. The complexes according to the invention can of course also be used in the hydroamination of non-prochiral olefins; however, since in this case achiral products are formed, the use of chiral diphosphine ligands does not confer any particular advantages.

For use as catalyst or catalyst precursor, it is not necessary to isolate the complexes according to the invention, but they can optionally also be prepared in situ.

The hydroamination can either be intermolecular or intramolecular. Thus, for example, o-allyl- and/or o-propenylanilines can give 2-methylindolines. The hydroamination normally proceeds in such a way that the amino group is added to the less sterically hindered carbon atom in the case of olefins with the double bond between non-equivalent carbon atoms. If two diastereomeric addition products are possible, as is the case for example with norbornenes, then the sterically more favorable (exo-)isomer is usually formed.

The asymmetric hydroamination is preferably carried out in the presence of fluoride ions. It has been found that this considerably increases both the reactivity and the optical yield.

A preferred embodiment of the asymmetric hydroamination is a process for the preparation of optically active amines of the general formula:

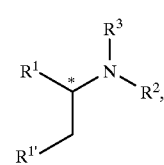

II in which the asterisk (*) designates an asymmetric center. The radicals R$^1$ and R$^{1'}$ are either independently of one another in each case an optionally substituted C$_{1-6}$-alkyl, aryl, arylalkyl, heteroaryl or (heteroaryl)alkyl group, with the proviso that R$^1$ is not R$^{1'}$—CH$_2$— (since in this case the asymmetric center disappears), or R$^1$ and R$^{1'}$, together with the carbon atoms in between, form a prochiral mono- or bicyclic cycloaliphatic system. R$^2$ is an optionally substituted aryl or acyl group and R$^3$ is hydrogen, an optionally substituted acyl, alkanesulfonyl or arenesulfonyl group. The optically active amines (II) are prepared according to the invention by reacting an olefin of the general formula:

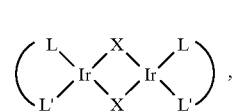

III in which R$^1$ and R$^{1'}$ are as defined above, in the presence of a chiral binuclear iridium (I) phosphine complex of the general formula:

I in which X is fluorine, chlorine, bromine or iodine, and

is in each case a chiral bidentate diphosphine ligand, with an amine or amide of the general formula R$^2$—NH—R$^3$ (IV), in which R$^2$ and R$^3$ are as defined above.

C$_{1-6}$-Alkyl groups in the above statements and in the text below are taken to mean all linear and branched primary, secondary or tertiary alkyl groups having 1 to 6 carbon atoms, i.e., for example, methyl, ethyl, propyl, isopropyl, butyl, isobutyl, tert-butyl, pentyl and hexyl. Correspondingly, C$_{1-6}$-alkoxy groups are taken to mean the groups comprising C$_{1-6}$-alkyl and oxygen. Mono- or bicyclic cycloaliphatic systems are in particular taken to mean those systems which consist of one or two rings each of which has from 3 to 7 ring carbon atoms. In the case of bicyclic systems, the rings may have the same or a different number of members and an either be condensed or else bridged or spiro-linked. The mono- or bicyclic systems may likewise carry functional groups and/or substituents.

Aryl groups are taken to mean mono- or polycyclic aromatic radicals, in particular groups such as phenyl or naphthyl.

Heteroaryl groups are correspondingly taken to mean mono- or polycyclic aromatic radicals carrying one or more heteroatoms, in particular groups such as furyl, thiophenyl, pyrrolyl, pyridyl, pyrimidyl or indolyl.

Correspondingly, arylalkyl groups and (heteroaryl)alkyl groups are taken to mean alkyl groups in which a hydrogen atom is replaced by one of the aryl groups or heteroaryl groups defined above, i.e., for example, benzyl, phenethyl or furylmethyl (furfuryl). All of these groups may also carry one or more identical or different substituents. Suitable substituents here and in the groups referred to above as "optionally substituted" are all those which are stable under the reaction conditions and react neither with the amino group nor with the olefinic double bond or the iridium complex. In particular, these may be, for example, $C_{1-4}$-alkyl groups, halogens or $C_{1-4}$-alkoxy groups.

Acyl groups are taken to mean both alkanoyl groups, in particular $C_{1-6}$-alkanoyl, and also aroyl groups, such as, benzoyl or substituted benzoyl.

Sulfonyl groups are taken to mean both alkanesulfonyl groups and also arenesulfonyl groups, in particular $C_{1-6}$-alkanesulfonyl, for example, methanesulfonyl ("mesyl"), and optionally substituted benzenesulfonyl, for example, p-toluenesulfonyl ("tosyl").

It has been shown that strained cyclic olefins in particular, such as, norbornene or cyclopropenone, give good results.

Among the amines (IV), preference is given to those which can be deprotonated relatively easily, i.e., aromatic amines or N-acyl or N-sulfonylamines (or amides or sulfonamides). When primary amides are used, N-acylamines (II, $R^2$=acyl, $R^3$=H) are formed, which can be hydrolyzed to primary amines.

A further preferred embodiment of the asymmetric hydroamination is a process for the preparation of optically active indolines of the general formula:

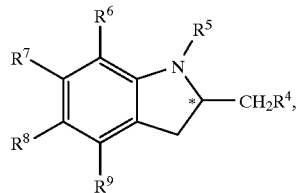

V in which $R^4$ is hydrogen or a $C_{1-4}$-alkyl group, $R^5$ has one of the meanings given above for $R^2$ and $R^3$, and $R^6$ to $R^9$ independently of one another are hydrogen, $C_{1-6}$-alkyl or $C_{1-6}$-alkoxy. For this purpose an o-alkenylaniline of the general formula:

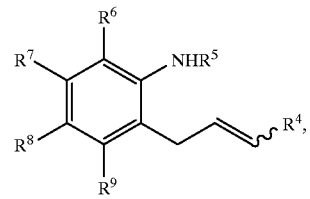

VI in which $R^4$ to $R^9$ are as defined above, is cyclized in the presence of a chiral binuclear iridium (I) phosphine complex of the general formula:

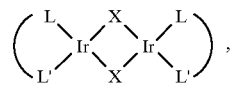

I in which X is fluorine, chlorine, bromine or iodine, and

is in each case a chiral bidentate diphosphine ligand.

As already mentioned, the process according to the invention for the preparation of optically active amines (II) or indolines (V) is preferably carried out in the presence of fluoride ions. The fluoride ions are preferably in "naked" form, i.e., are not solvated or in the form of an ion pair. Examples of fluoride ion sources are thallium(I) fluoride or an alkali metal fluoride whose cation has been complexed by a suitable crown ether or cryptand. Particular preference is given to fluorides or complex fluorides of organic bases, such as, tetramethylammonium fluoride or tetrabutylammonium triphenyldifluorosilicate. A very particularly preferred source of "naked" fluoride ions is 1,1,1,3,3,3-hexakis (dimethylamino)diphosphazenium fluoride.

In the process according to the invention for the preparation of optically active amines (II) or indolines (V), the catalysts used are preferably those iridium (I) phosphine complexes (I) in which the chiral bidentate diphosphine ligands are chosen from the group consisting of (R)-2,2'-bis (diphenylphosphino)-1,1'-binaphthalene, (S)-2,2'-bis (diphenylphosphino)-1,1'-binaphthalene, (R)-2,2'-bis (diphenylphosphino-6,6'-dimethyl-1,1'-biphenyl, (S)-2,2'-bis(diphenylphosphino)-6,6'-dimethyl-1,1'-biphenyl, 1-[1 (R)-(dicyclohexylphosphino)ethyl]-2(S)-(diphenylphosphino)ferrocene, 1-[1(S)-(dicyclohexylphosphino)ethyl]-2(R)-(diphenylphosphino) ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino) ferrocene, 1-{1(R)-[bis(3,5-dimethylphenyl)phosphino] ethyl}-2(S)-(diphenylphosphino)ferrocene and 1-{1(S)-[bis (3,5-dimethylphenyl)phosphino]ethyl}-2(R)-(diphenylphosphino)-ferrocene.

Other preferred catalysts are those iridium (I) phosphine complexes in which X is chlorine.

In a preferred embodiment of the process according to the invention for the preparation of the optically active amines (II), $R^1$ and $R^{1'}$ together form a cyclopentane-1,3-diyl group, i.e., norbornene (bicyclo[2.2.1]hept-2-ene) is used as olefin (III).

In a further preferred embodiment of the process according to the invention for the preparation of the optically active amines (II), $R^2$ is an optionally substituted phenyl group, i.e., an optionally substituted aniline is used as amine (IV).

The examples below illustrate the execution of the invention, without intending any limitation thereto. All operations were carried out under protective gas and with the exclusion of moisture.

EXAMPLE 1

Di-μ-chlorotetrakis($\eta^2$-cyclooctene)diiridium(I)

12 ml of cyclooctene was added to a suspension of 6.08 g (10 mmol) of ammonium hexachloroiridate (IV) in 30 ml of isopropyl alcohol and 90 ml of water, and the whole was refluxed for 3 hours. After the mixture had cooled to room temperature, the supernatant solution was decanted off, and the orange-yellow residue was digested in 30 ml of ethanol. This mixture was cooled to 0° C., and filtered over Celite under argon. The resultant product was dried overnight under a high vacuum, and stored at −25° C. with the exclusion of oxygen and light. Data concerning the product was:

$^1$H NMR (CDCl$_3$, 250 MHz): δ 1.2–1.7 (8H); 2.2–2.4 (6H) $^{13}$C NMR (CDCl$_3$, 60 MHz): δ 26.4; 29.9; 30.3; 63.4.

EXAMPLE 2 cis- and trans-Di-μ-chlorobis{1-[1(R)-(dicyclohexylphosphino)ethyl]-2(S)-(diphenylphosphino)ferrocene}-1$\kappa^2$P$^1$, P$^2$; 2$\kappa^2$P$^{1'}$, P$^{2'}$-diiridium(I)

Ethene was passed through a yellow suspension of 2.961 g (3.305 mmol) of di-μ-chlorotetrakis($\eta^2$-cyclooctene)diiridium(I) in 30 ml of heptane at 0° C. for 10 min. The mixture was cooled to −78° C., and 120 ml of pentane was added with stirring, with the formation of a whitish solid. The supernatant solution was decanted off and 100 ml of toluene was added. A solution of 1-[1(R)-(dicyclohexylphosphino)ethyl]-2(S)-(diphenylphosphino)ferrocene was added dropwise to the yellowish mixture at −78° C. over the course of 15 minutes. The reaction mixture was slowly allowed to reach room temperature overnight, excess ethene being able to escape. The mixture was then evaporated under reduced pressure, and the residue was recrystallized from benzene/pentane. Drying under reduced pressure gave a fine orange-colored powder. According to $^1$H NMR, the product contained half a molecule of each of benzene and pentane per binuclear complex, which agreed with the result of the elemental analysis. The yield of the product was 3.05 g (84 percent). Other data concerning the product is:

C$_{72}$H$_{88}$Cl$_2$Fe$_2$Ir$_2$P$_4$·½C$_6$H$_6$·½C$_5$H$_{12}$: Calc. C 54.13 H 5.69 Found C 54.30 H 5.98 $^{31}$P{$^1$H} NMR (C$_6$D$_6$, 100 MHz): AA'XX' system, two isomers. δ-0.13 ($^2$J$_{pp'}$+$^4$J$_{pp'}$= 29.9 Hz) (isomer A); 0.07 ($^2$J$_{pp'}$+$^4$J$_{pp'}$=35.2 Hz) (isomer B) 30.16 ($^2$J$_{pp'}$+$^4$J$_{pp'}$=30.1 Hz) (isomer A); 30.95 ($^2$J$_{pp'}$+$^4$J$_{pp'}$= 35.0 Hz) (isomer B). $^1$H NMR (C$_6$D$_6$, 250 MHz): δ 0.85–2.30 (m, 48H); 2.50–2.75 (m, 2H); 2.75–3.20 (m, 2H); 3.55 and 3.63 (2 s, 10H); 3.75–4.00 (m, 2H); 3.97 (m, 2H); 4.08 (m, 2H); 4.25–4.35 (m, 2H); 7.00–7.40 (m, 12H); 7.55–7.75 (m, 2H); 7.75–7.85 (m, 2H); 8.30–8.45 (m, 2H); 8.60–8.75 (m, 2H).

EXAMPLE 3 cis- and trans-Di-μ-chlorobis{1-[1(R)-(diphenylphosphino)ethyl]-2(S)-(diphenylphosphino)ferrocene}-1$\kappa^2$P$^1$,P$^2$;2$\kappa^2$P$^{1'}$,P$^{2'}$-diiridium(I)

A solution of 3.27 g (5.62 mmol) of 1-[1(R)-(diphenylphosphino)ethyl]-2(S)-(diphenylphosphino)ferrocene in 20 ml of benzene was added dropwise to a pale orange suspension of di-μ-chlorotetrakis($\eta^2$-cyclooctene)diiridium(I) in 20 ml of benzene over the course of 20 min. The reaction mixture was left to stand overnight at 4° C, during which an orange-colored microcrystalline precipitate formed. This was filtered off and dried under reduced pressure for 24 hours. According to $^1$H NMR, the product contained 1½ molecules of benzene per binuclear complex, which agreed with the results of the elemental analysis. The yield of the product was 3.95 g (85 percent). Other data concerning the product is:

C$_{72}$H$_{88}$Cl$_2$Fe$_2$Ir$_2$P$_4$·1.5 C$_6$H$_6$: Calc. C 56.00 H 4.24 Found C 56.03 H 4.33 $^{31}$P{$^1$H} NMR (THF-d$_8$, 100 MHz): AA'XX' system, two isomers. δ-2.82 ($^2$J$_{pp'}$+$^4$J$_{pp'}$=38.5 Hz) (isomer A); −1.98 ($^2$J$_{pp'}$+$^4$J$_{pp'}$=30.7 Hz) (isomer B); 23.35 ($^2$J$_{pp'}$+$^4$J$_{pp'}$=38.5 Hz) (isomer A); 24.34 ($^2$J$_{pp'}$+$^4$J$_{pp'}$=30.7 Hz) (isomer B). $^1$H NMR (THF-d$_8$, 250 MHz): δ 0.60–0.85 (m, 6H); 3.43 and 3.50 (2 s, 10H); 3.50–3.90 (m, 4H); 4.10 (m, 2H); 4.19 (m, 2H); 6.85–7.65 (m, 28H); 8.00–8.35 (m, 10H); 8.50–8.65 (m, 2H).

EXAMPLE 4 cis- and trans-Di-μ-chlorobis(1-{1(R)-[bis(3,5-dimethylphenyl)phosphino]ethyl}-2(S)-(diphenylphosphino)-ferrocene)-1$\kappa^2$P$^1$,P$^2$;2$\kappa^2$P$^{1'}$,P$^{2'}$-diiridium(I)

A solution of 2.001 g (3.133 mmol) of 1-{1(R)-[bis(3,5-dimethylphenyl)phosphino]ethyl}-2(S)-(diphenylphosphino)ferrocene in 40 ml of benzene was added dropwise to a pale orange suspension of 1.416 g (1.566 mol) of di-μ-chlorotetrakis($\kappa^2$-cyclooctene)diiridium (I) in 40 ml of benzene with stirring over the course of 20 min, during which a deep-red clear solution formed. After a further 15 min., the solvent was distilled off under reduced pressure. The orange residue was washed with pentane and dried under reduced pressure. The yield of the product was 2.40 g (88 percent) of yellow powder. Other data concerning the product is:

C$_{80}$H$_{80}$Cl$_2$Fe$_2$Ir$_2$P$_4$: Calc. C 55.46 H 4.65 Found C55.18 H4.80 $^{31}$P{$^1$H} NMR (C$_6$D$_6$, 100 MHz): AA'XX' system, two isomers. δ-4.22 ($^2$J$_{pp'}$+$^4$J$_{pp'}$=38.3 Hz) (isomer A); −1.01 ($^2$J$_{pp'}$+$^4$J$_{pp'}$=30.6 Hz) (isomer B); 22.70 ($^2$J$_{pp'}$+$^4$J$_{pp'}$=38.2 Hz) (isomer A); 26.73 ($^2$J$_{pp'}$+$^4$J$_{pp'}$=30.6 Hz) (isomer B). $^1$NMR (C$_6$D$_6$, 250 MHz): δ 1.05–1.20 (m, 6H, isomer A); 1.25–1.35 (m, 6H, isomer B); 2.12 (s, 12H, isomer B); 2.17 (s, 12H, isomer B); 2.22 (s, 12H, isomer A); 2.38 (s, 12H, isomer A); 3.57 (s, 1OH, isomer B); 3.68 (s, 10H, isomer A); 3.75–3.40 (m, 8H, isomer A+B); 6.75–8.55 (m, 32H, isomers A+B).

EXAMPLE 5 cis- and trans-Di-μ-chlorobis{1-[1(R)-[diphenyl)phosphino)ethyl]-2(S)-(di-tert-butylphosphino)-ferrocene}-1$\kappa^2$P$^1$,P$^2$;2$\kappa^2$P$^{1'}$,P$^{2'}$-diiridium(I)

Ethylene was passed through a suspension of 264.4 mg (275 μmol) of di-μ-chlorotetrakis($\eta^2$-cyclooctene)diiridium (I) in 2 ml of heptane at 0° C. for 10 min. After the suspension had cooled to −78° C., 2 ml of hexane was added with stirring, and after stirring for a further 10 min the supernatant suspension was decanted off. The slightly yellowish precipitate was dried briefly under a high vacuum and then dissolved in 2 ml of toluene. A solution of 1-[1 (R)-(diphenylphosphino)ethyl]-2(S)-(di-tert-butylphosphino)ferrocene (300.4 mg, 0.55 mmol) in 2 ml of toluene was added dropwise to the resultant cloudy yellow solution over the course of 15 min, the temperature being maintained below −73° C. The mixture was then warmed to room temperature overnight, it being ensured that the excess ethylene was able to escape. The volatile constituents were removed under reduced pressure, and the residue was washed with hexane and dried. The yield of the product was 329 mg (77 percent based on the diphosphine used) of an orange powder. Other data concerning the product is:

$^{31}P$ NMR ($C_6D_6$, 100 MHz): two isomers. δ-13.5 (d, $^2J_{pp'}+^4J_{pp'}$=20.5 Hz); 18.9 (d, $^2J_{pp'}+^4J_{pp'}$=19.8 Hz); 24.3 (d, $^2J_{pp'}+^4J_{pp'}$=33.3 Hz); 26.5 (d, $^2J_{pp'}+^4J_{pp'}$=33.2 Hz).

EXAMPLE 6 cis- and trans-Di-μ-chlorobis{1-[1(R)-(9-phosphabicyclo[3.3.1nonan-9-yl)ethyl]-2(S)-(diphenylphosphino)ferrocene}-1κ²P¹,P²;2κ²P¹',P²'-diiridium(I)

Following the procedure in Example 5, 830 mg (0.9 mmol) of di-μ-chlorotetrakis($\eta^2$-cyclooctene)diiridium(I) was reacted with 1.00 g (1.86 mmol) of 1-[1(R)-(9-phosphabicyclo[3.3.1]nonan-9-yl)ethyl]-2(S)-(diphenylphosphino)ferrocene. Data concerning the product is:

$^{31}P$ NMR ($C_6D_6$, 100 MHz): two isomers δ-5.2 (d, $^2J_{pp'}+^4J_{pp'}$=39.3 Hz); −1.8 (d, $^2J_{pp'}+^4J_{pp'}$=39.0 Hz); 1.0 (d, $^2J_{pp'}+^4J_{pp'}$=42.5 Hz); 3.4 (d, $^2J_{pp'}+^4J_{pp'}$=42.1 Hz).

EXAMPLE 7

Di-μ-chlorobis[(S)-2,2'-bis(diphenylphosphino)-1,1'-binaphthalene]-1κ²P¹, P²; 2κ²P¹',P²'-diiridium(I)

A suspension of 484 mg (777 μmol) of (S)-2,2'-bis(diphenylphosphino)-1,1'-binaphthalene in 4 ml of benzene was added dropwise with stirring to a suspension of 349 mg (389 μmol) of di-μ-chlorotetrakis($\eta^2$-cyclooctene)diiridium (I) in 4 ml of benzene, as a result of which a deep-red solution formed. After 20 hours at room temperature, the solvent was distilled off under reduced pressure. The residue was washed with 2×4 ml of cold pentane and dried under reduced pressure. According to $^1H$ NMR, the product contained half a molecule of pentane per binuclear complex, which agreed with the result of the elemental analysis. The yield of the product was 580 mg (88 percent) of red powder. Other data concerning the product is:

$C_{88}H_{64}Cl_2Ir_2P_4 \cdot \frac{1}{2} C_5H_{12}$: Calc. C 62.59 H 4.06 Found C 62.99 H 4.01 $^{31}P\{^1H\}$ NMR ($C_6D_6$): δ 14.14 (s). $^1H$ NMR ($C_6D_6$): δ 6.67–8.53 (m).

The structure of the complex was confirmed by singe crystal X-ray structure analysis. Ruby-red monoclinic single crystals (each containing 1 molecule of diethyl ether and tetrahydrofuran) were obtained by diffusing diethyl ether and tetrahydrofuran into a saturated solution in toluene.

Crystallographic data of $C_{88}H_{64}Cl_2Ir_2P_4 \cdot C_4H_{10}O \cdot C_4H_8O$ (at −30° C.): a=17.0108 Å; b=13.6600 Å; c=18.9391 Å β=115.8189° Space group P2$_1$ (No. 4); Z=2.

EXAMPLE 8

Di-μ-chlorobis[(R)-2,2'-bis(diphenylphosphino)-6,6'-dimethyl-1,1'-biphenyl]-1κ²P¹,P²;2κ²P¹',P²'-diiridium(I)

A solution of 538 mg (997 μmol) of (R)-2,2'-bis(diphenylphosphino)-6,6'-dimethyl-1,1'-biphenyl in 1.5 ml of benzene was added dropwise with stirring to a suspension of 438 mg (488 μmol) of di-μ-chlorotetrakis($\eta^2$-cyclooctene)diiridium(I) in 1.5 ml of benzene, as a result of which a deep-red solution formed. After 20 hours at room temperature, the solvent was distilled off under reduced pressure. The residue was washed with 5×1 ml of cold pentane and dried under reduced pressure. The yield of the product was 659 mg (87 percent) of red powder. Other data concerning the product is:

$C_{78}H_{64}Cl_2Ir_2P_4$: Calc. C 58.64 H 4.14 Found C 58.41 H 3.91 $^{31}P\{^1H\}$ NMR ($C_6D_6$): δ 13.46 (s). $^1H$ NMR ($C_6D_6$): δ 1.43 (s, 12H); 6.51–8.33 (m, 52H).

EXAMPLE 9 exo-N-Phenylbicyclo[2.2.1]heptan-2-amine 0.12 ml of a solution of 1,1,1,3,3,3-hexakis(dimethylamino)-diphosphazenium fluoride (about 0.5M in benzene, about 60 μmol) was added using a syringe to a mixture of 575 mg (6.11 μmol) of norbornene and 569 mg (6.11 μmol) of aniline. The resultant solution was added to 53.0 mg (30.5 μmol) of cis- and trans-di-μ-chlorobis{1-[1(R)-(dicyclohexylphosphino)ethyl]-2(S)-diphenylphosphino)ferrocene}-1κ²P¹,P²;2κ²P¹',P²'-diiridium(I) (from Example 1, as toluene solvate), as a result of which a clear orange solution formed. This solution was stirred in a closed vessel at 50° C. for 72 hours and then quenched by admitting air. The product was purified by column chromatography on silica get (I=10 cm, d=2 cm, ethyl acetate/hexane 1:10). The yield of the product was 814 mg (80 percent) of a pale yellow oil. The optical yield was determined by HPLC (stationary phase: Daicel Chiralcel® OJH, mobile phase: hexane/2-propanol 90:10). The retention times were 15:5 min for the (2R)-enantiomer and 17.2 min for the (2S)-enantiomer. An ee value of 50 percent in favor of the (2R)-enantiomer was found.

EXAMPLES 10 to 23 exo-N-Phenylbicyclo[2.2.1]heptan-2-amine

The procedure used was that described in Example 6, but the iridium complexes, reaction temperatures and amounts of fluoride used were varied. The results are given in Table 1 below:

TABLE 1

| Example No. | Catalyst from Example | T [°C.] | [F]/[Ir] | Yield, [%]$^c$ | ee[%] (config.) |
|---|---|---|---|---|---|
| 10 | 2$^a$ | 50 | 0 | 12 | 51 (2S) |
| 11 | 2$^a$ | 50 | 0.25 | 76 | 31 (2R) |
| 12 | 2$^a$ | 50 | 4 | 51 | 16 (2R) |
| 13 | 2$^a$ | 25 | 1 | 12 | 60 (2R) |
| 14 | 2$^a$ | 75 | 1 | 81$^d$ | 38 (2R) |
| 15 | 3$^a$ | 50 | 1 | 27 | 9 (2R) |
| 16 | 4$^a$ | 50 | 1 | 36 | 26 (2R) |
| 17 | 7$^b$ | 50 | 0 | 12 | 57 (2R) |
| 18 | 7$^b$ | 75 | 2 | 45 | 78 (2R) |
| 19 | 7$^b$ | 75 | 4 | 22 | 95 (2R) |
| 20 | 8$^b$ | 50 | 1 | 13 | 51 (2S) |
| 21 | 8$^b$ | 75 | 1 | 37 | 43 (2S) |
| 22 | 8$^b$ | 75 | 2 | 27 | 69 (2S) |
| 23 | 8$^b$ | 75 | 4 | 24 | 92 (2S) |

Notes:
$^a$: 1 mol % Ir.
$^b$: 2 mol % Ir.
$^c$: isolated yield.
$^d$: 24 hour reaction time.

EXAMPLE 24 p-Toluenesulfonic acid o-allylanilide 10.8 g (56.8 mmol) of p-toluenesulfonyl chloride and 6 ml of pyridine were added to a solution of 7.56 g (56.8 mmol)

of o-allylaniline (obtainable from N-allylaniline by BF$_3$-catalyzed rearrangement) in 50 ml of dichloromethane, and the mixture was refluxed for 2 hours. The solvent was then distilled off, and the yellow viscous residue was shaken with 1M sodium hydroxide solution. The phases were separated, and the aqueous phase was acidified and extracted with toluene. The yield of the product was 10.0 g (61.3 percent) of colorless oil, solidified at 4° C. Other data concerning the product is:

$^1$H NMR (CDCl$_3$, 250 MHz): δ 2.40 (s, 3H); 3.02 (d, J=6.0 Hz, 1H); 4.94 (dd, J=17.0 and 1.8 Hz, 1H); 5.09 (dd, J=10.3 and 1.5 Hz, 1H); 5.78 (tdd, J=6.0; 17.3 and 10.3 Hz, 1H); 6.63 (s, 1H); 7.0–7.7 (m, 8H). $^{13}$C NMR (CDCl$_3$, 60 MHz): δ 21.5; 38.0; 117.1; 124.4; 126.2; 127.1; 127.7; 129.6; 130.5; 135.5.

EXAMPLE 25

Methanesulfonic acid o-allylanilide

Following the procedure in Example 24, 2.31 g (17.3 mmol) of o-allylaniline, 1.5 ml of methanesulfonyl chloride and 1.5 ml of pyridine in 20 ml of benzene gave a viscous oil, which was purified using flash chromatography (silica gel 60, eluent toluene/ethyl acetate 7:1). The yield of the product was 1.37 g (37 percent, based on o-allylaniline). Other data concerning the product is:

$^1$H NMR (CDCl$_3$, 250 MHz): δ 3.01 (s, 3H); 3.44 (d, J=6.0Hz, 1H); 5.08 (dd, J=17.3 and 1.5 Hz, 1H); 5.19 (dd, J=10.3 and 1.5 Hz, 1H); 5.96 (tdd, J=6.0; 17.3 and 10.3 Hz, 1H); 6.44 (s, 1H); 7.2–7.5 (m, 4H). $^{13}$C NMR (CDCl$_3$, 60 MHz): 37; 42; 117; 128; 129; 136.

EXAMPLES 26 to 29

2-Methyl-N-p-toluenesulfonylindoline

General Instructions p-Toluenesulfonic acid o-allylanilide (100 mg) was dissolved with 5 mg (about 1 mol percent) of the iridium (I) phosphine complex in 0.1 ml of a 0.6M solution of 1,1,1,3,3,3-hexakis(dimethylamino)diphosphazenium fluoride in benzene and then transferred with 0.5 ml of toluene to a Schlenk flask. This solution was stirred at the corresponding reaction temperature for the duration of the reaction. The solvent was then distilled off under reduced pressure, and the residue was filtered with hexane/ethyl acetate over silica gel 60. After evaporation of the eluent and drying under a high vacuum, the product ratios were determined by integration of the signals in the $^1$H NMR spectrum. To determine the ee values ("enantiomeric excess"), the p-toluenesulfonyl group was cleaved off using HBr/acetic acid in phenol at 80° C. The reaction mixture was then taken up in toluene, and the solution was washed with sodium hydroxide solution and saturated sodium carbonate solution, dried over magnesium sulfate and evaporated under reduced pressure. The residue was distilled in a bulb-tube (160° C., about 10 mbar). The distillate was separated into the enantiomers by HPLC (Chiralcel® OD-H, 4.6×250 mm, particle size 5 μm, eluent hexane/isopropyl alcohol 99:1 with 0.3 percent of diethylamine, flow rate 0.5 ml/min, UV detection at 300 nm).

The results are given in Table 2 below. The conversion in each case was 100 percent.

TABLE 2

| Example No. | Catalyst from Example | T [°C.] | t | Yield, [%] | ee, [%] |
|---|---|---|---|---|---|
| 26 | 5 | 120 | 18 h | 18.6 | 47.4 |
| 27 | 2 | 120 | 18 h | 25.5 | 57.3 |
| 28 | 5 | 80 | 14 d | 15.3 | 35.7 |
| 29 | 2 | 80 | 14 d | 26.1 | 57.9 |

EXAMPLES 30 to 32

2-Methyl-N-p-methanesulfonylindoline

The procedure used was that described in the general instructions for Examples 26 to 29 but using methanesulfonic acid o-allylanilide instead of p-toluenesulfonic acid o-allylanilide. The results are given in Table 3 below.

TABLE 3

| Example No. | Catalyst from Example | T [°C.] | t | Conversion % | Yield, [%] | ee, [%] |
|---|---|---|---|---|---|---|
| 30 | 5 | 25 | 3–4 d | 26.5 | 8.2 | 52 |
| 31 | 5 | 120 | 18 h | 100 | 21.6 | 35.3 |
| 32 | 2 | 25 | 3–4 d | 100 | 14 | 43.6 |

What is claimed is:

1. An iridium (I) phosphine complex of the formula:

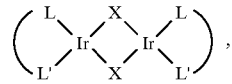

I in which X is fluorine, chlorine, bromine or iodine, and

is in each case a chiral bidentate diphosphine ligand, including cis-isomer thereof, trans-isomer thereof and isomeric mixtures thereof.

2. The iridium (I) phosphine complex according to claim 1 which is in solid form.

3. The iridium (I) phosphine complex according to claim 2, wherein the chiral bidentate diphosphine ligand is a 1,2-disubstituted ferrocene with the phosphino groups on the two substituents.

4. The iridium (I) phosphine complex according to claim 2, wherein the chiral bidentate diphosphine ligand is selected from the group consisting of (R)-2,2'-bis(diphenylphosphino)-1,1'-binaphthalene, (S)-2,2'-bis(diphenylphosphino)-1,1'-binaphthalene, (R)-2,2'-bis(diphenylphosphino)-6,6'-dimethyl-1,1'-biphenyl, (S)-2,2'-bis(diphenylphosphino)-6,6'-dimethyl-1,1'-biphenyl, 1-[1(R)-(dicyclohexylphosphino)ethyl]-2 (S)-(diphenylphosphino)ferrocene, 1-[1(S)-(dicyclohexylphosphino)ethyl]-2(R)-(diphenylphosphino)ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino)ferrocene, 1-[1(R)-(diphenylphosphino)ethyl]-2(S)-(di-tert-butylphosphino)ferrocene, 1-[1(S)-(diphenylphosphino)

ethyl]-2(R)-(di-tert-butylphosphino)ferrocene, 1-{1(R)-[bis (3,5-dimethylphenyl)phosphino]ethyl}-2(S)- (diphenylphosphino)ferrocene, 1-{1(S)-[bis(3,5-dimethylphenyl)phosphino]ethyl}-2(R)- (diphenylphosphino)-ferrocene, 1-{1(R)-[bis(4-tert-butylphenyl)phosphino]ethyl}-2(S)-(diphenylphosphino) ferrocene, 1-{1(S)-[bis(4-tert-butylphenyl)phosphino] ethyl}-2(R)-(diphenylphosphino)ferrocene, 1-[1(S)-(9-phosphabicyclo[3.3.1]nonan-9-yl)ethyl]-2(R)- (diphenylphosphino)ferrocene and 1-[1(R)-(9-phosphabicyclo[3.3.1]nonan-9-yl)ethyl]-2(S)- (diphenylphosphino ferrocene.

5. The iridium (I) phosphine complex according to claim 4, wherein X is chlorine.

6. The iridium (I) phosphine complex according to claim 1, wherein the chiral bidentate diphosphine ligand is a 1,2-disubstituted ferrocene with the phosphine groups on the two substituents.

7. The iridium (I) phosphine complex according to claim 1, wherein the chiral bidentate diphosphine ligand is chosen from the group consisting of (R)-2,2'-bis (diphenylphosphino)-1,1'-binaphthalene, (S)-2,2'-bis (diphenylphosphino)-1,1'-binaphthalene, (R)-2,2'-bis (diphenylphosphino-6,6'-dimethyl-1,1'-biphenyl, (S)-2,2'-bis(diphenylphosphino)-6,6'-dimethyl-1,1'-biphenyl, 1-[1 (R)-(dicyclohexylphosphino)ethyl]-2(S)- (diphenylphosphino)ferrocene, 1-[1(S)- (dicyclohexylphosphino)ethyl]-2(R)-(diphenylphosphino) ferrocene, 1-[1(R)-(diphenylphosphino)ethyl]-2(S)- (diphenylphosphino)ferrocene, 1-[1(S)- (diphenylphosphino)ethyl]-2(R)-(diphenylphosphino) ferrocene, 1-[1(R)-(diphenylphosphino)ethyl]-2-(S)-(di-tert-butylphosphino)ferrocene, 1-[1(S)-diphenylphosphino) ethyl]-2(R)-(di-tert-butylphosphino)ferrocene, 1-[1(R)-[bis (3,5-dimethylphenyl)phosphino]ethyl}-2(S)- (diphenylphosphino)ferrocene, 1-{1(S)-[bis(3,5-dimethylphenyl)phosphino]ethyl}-2(R)- (diphenylphosphino)-ferrocene, 1-{1(R)-[bis(4-tert-butylphenyl)phosphino]ethyl}-2(S)-(diphenylphosphino) ferrocene, 1-{1(S)-[bis(4-tert-butylphenyl)phosphino] ethyl}-2(R)-(diphenylphosphino)ferrocene, 1-[1(S)-(9-phosphabicyclo[3.3.1]nonan-9-yl)ethyl]-2(R)- (diphenylphosphino)ferrocene and 1-[1(R)-(9-phosphabicyclo[3.3.1]nonan-9-yl)ethyl]-2(S)- (diphenylphosphino)ferrocene.

8. The iridium (I) phosphine complex according to claim 1, wherein X is chlorine.

9. A process for the preparation of an iridium (I) phosphine complex according to claim 1, wherein an iridium (I) complex of the formula [IrX(coe)$_2$]$_2$ or [IrX(C$_2$H$_4$)$_4$], in which X is fluorine, chlorine, bromine or iodine and coe is cyclooctene, in a nonpolar solvent is reacted with the corresponding chiral bidentate diphosphine.

10. A process for the preparation of an iridium (I) phosphine complex according to claim 5 wherein an iridium (I) complex of the formula [IrX(coe)$_2$]$_2$ or [IrX(C$_2$H$_4$)$_4$], in which X is fluorine, chlorine, bromine or iodine and coe is cyclooctene, in a nonpolar solvent is reacted with the corresponding chiral bidentate diphosphine.

11. A process comprising using an iridium (I) phosphine complex according to claim 1 as catalyst in the asymmetric hydroamination of a prochiral olefin.

12. The process according to claim 11, wherein the hydroamination is carried out in the presence of fluoride ions.

13. A process comprising using an iridium (I) phosphine complex according to claim 5 as catalyst in the asymmetric hydrogenation of the prochiral olefin.

14. The process according to claim 13, wherein the hydrogenation is carried out in the presence of fluoride ions.

15. A process for the preparation of an optically active amine of the formula:

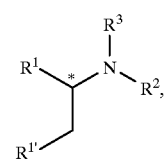

in which either $R^1$ and $R^{1'}$ independently of one another are in each case an optionally substituted $C_{1-6}$-alkyl group, an optionally substituted aryl group, an optionally substituted arylalkyl group, an optionally substituted heteroaryl group or an optionally substituted (heteroaryl)alkyl group, with the proviso that $R^1$ is not $R^{1'}$—$CH_2$—, or $R^1$ and $R^{1'}$, together with the carbon atoms in between, form a prochiral mono- or bicyclic cycloaliphatic system, $R^2$ is an optionally substituted aryl or acyl group, and $R^3$ is hydrogen, an optionally substituted acyl, alkanesulfonyl or arenesulfonyl group, comprising reacting an olefin of the formula:

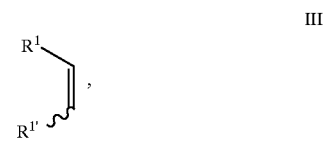

in which $R^1$ and $R^{1'}$ are as defined above, in the presence of a chiral binuclear iridium (I) phosphine complex of the formula:

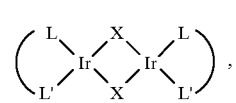

in which X is fluorine, chlorine, bromine or iodine, and

is in each case a chiral bidentate diphosphine ligand, with an amine or amide of the formula $R^2$—NH—$R^3$ (IV), in which $R^2$ and $R^3$ are as defined above.

16. The process according to claim 15, wherein the reaction is carried out in the presence of fluoride ions.

17. The process according to claim 16, wherein the fluoride ions are used in the form of the fluoride of an organic base.

18. The process according to claim 17, wherein the fluoride of an organic base is 1,1,1,3,3,3-hexakis (dimethylamino)diphosphazenium fluoride.

19. The process according to claim 18, wherein the chiral bidentate diphosphine ligand is selected from the group consisting of (R)-2,2'-bis(diphenylphosphino)-1,1'-binaphthalene, (S)-2,2'-bis(diphenylphosphino)-1,1'-binaphthalene, (R)-2,2'-bis(diphenylphosphino)-6,6'-dimethyl-1,1'-biphenyl, (S)-2,2'-bis(diphenylphosphino)-6, 6'-dimethyl-1,1'-biphenyl, 1-[1(R)-(dicyclohexylphosphino) ethyl]-2(S)-(diphenylphosphino)ferrocene, 1-[1(S)-

(dicyclohexylphosphino)ethyl]-2(R)-(diphenylphosphino) ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino) ferrocene, 1-[1(R)-(diphenylphosphino)ethyl]-2(S)-(di-tert-butylphosphino)ferrocene, 1-[1(S)-(diphenylphosphino) ethyl]-2(R)-(di-tert-butylphosphino)ferrocene, 1-{1(R)-[bis (3,5-dimethylphenyl)phosphino]ethyl}-2(S)-(diphenylphosphino)ferrocene, 1-{1(S)-[bis(3,5-dimethylphenyl)phosphino]ethyl}-2(R)-(diphenylphosphino)-ferrocene, 1-{1(R)-[bis(4-tert-butylphenyl)phosphino]ethyl}-2(S)-(diphenylphosphino) ferrocene, 1-{1(S)-[bis(4-tert-butylphenyl)phosphino] ethyl}-2(R)-(diphenylphosphino)ferrocene, 1-[1(S)-(9-phosphabicyclo[3.3.1]nonan-9-yl)ethyl]-2(R)-(diphenylphosphino)ferrocene and 1-[1(R)-(9-phosphabicyclo[3.3.1]nonan-9-yl)ethyl]-2(S)-(diphenylphosphino)ferrocene.

20. The process according to claim 19, wherein X is chlorine.

21. The process according to claim 20, wherein $R^1$ and $R^{1'}$ together form a cyclopentane-1,3-diyl group.

22. The process according to claim 21, wherein $R^2$ is an optionally substituted phenyl group.

23. The process according to claim 15, wherein the chiral bidentate diphosphine ligand is chosen from the group consisting of (R)-2,2'-bis(diphenylphosphino)-1,1'-binaphthalene, (S)-2,2'-bis(diphenylphosphino)-1,1'-binaphthalene, (R)-2,2'-bis(diphenylphosphino)-6,6'-dimethyl-1,1'-biphenyl, (S)-2,2'-bis(diphenylphosphino)-6,6'-dimethyl-1,1'-biphenyl, 1-[1(R)-(dicyclohexylphosphino) ethyl]-2(S)-(diphenylphosphino)ferrocene, 1-[1(S)-(dicyclohexylphosphino)ethyl]-2(R)-(diphenylphosphino) ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino) ferrocene, 1-[1(R)-(diphenylphosphino)ethyl]-2(S)-(di-tert-butylphosphino)ferrocene, 1-[1(S)-(diphenylphosphino) ethyl]-2(R)-(di-tert-butylphosphino)ferrocene, 1-{1(R)-[bis (3,5-dimethylphenyl)phosphino]ethyl}-2(S)-(diphenylphosphino)ferrocene, 1-{1(S)-[bis(3,5-dimethylphenyl)phosphino]ethyl}-2(R)-(diphenylphosphino)-ferrocene, 1-{1(R)-[bis(4-tert-butylphenyl)phosphino]ethyl}-2(S)-(diphenylphosphino) ferrocene, 1-{1(S)-[bis(4-tert-butylphenyl)phosphino]ethyl}-2(R)-(diphenylphosphino)ferrocene, 1-[1(S)-(9-phosphabicyclo[3.3.1]nonan-9-yl)ethyl]-2(R)-(diphenylphosphino)ferrocene and 1-[1(R)-(9-phosphabicyclo[3.3.1]nonan-9-yl)ethyl]-2(S)-(diphenylphosphino)ferrocene.

24. The process according to claim 15, wherein X is chlorine.

25. The process according to claim 15, wherein $R^1$ and $R^{1'}$ together form a cyclopentane-1,3-diyl group.

26. The process according to claim 15, wherein $R^2$ is an optionally substituted phenyl group.

27. A process for the preparation of an optically active indoline of the formula:

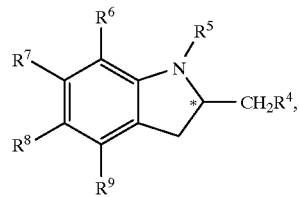

in which $R^4$ is hydrogen or a $C_{1-4}$-alkyl group, $R^5$ is hydrogen, an optionally substituted aryl group, an optionally substituted acyl group, an alkanesulfonyl group, or an arenesulfonyl group, and $R^6$ to $R^9$ independently of one another are hydrogen, $C_{1-6}$-alkyl or $C_{1-6}$-alkoxy, comprising cyclizing an o-alkenylaniline of the formula:

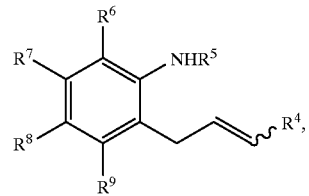

in which $R^4$ to $R^9$ are as defined above, in the presence of a chiral binuclear iridium (I) phosphine complex of the formula:

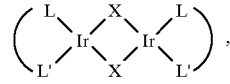

in which X is fluorine, chlorine, bromine or iodine, and

is in each case a chiral bidentate diphosphine ligand.

28. The process according to claim 27, wherein the reaction is carried out in the presence of fluoride ions.

29. The process according to claim 28, wherein the fluoride ions are used in the form of the fluoride of an organic base.

30. The process according to claim 29, wherein the fluoride of an organic base is 1,1,1,3,3,3-hexakis (dimethylamino)diphosphazenium fluoride.

31. The process according to claim 30, wherein the chiral bidentate diphosphine ligand is chosen from the group consisting of (R)-2,2'-bis(diphenylphosphino)-1,1'-binaphthalene, (S)-2,2'-bis(diphenylphosphino)-1,1'-binaphthalene, (R)-2,2'-bis(diphenylphosphino)-6,6'-dimethyl-1,1'-biphenyl, (S)-2,2'-bis(diphenylphosphino)-6,6'-dimethyl-1,1'-biphenyl, 1-[1(R)-(dicyclohexylphosphino) ethyl]-2(S)-(diphenylphosphino)ferrocene, 1-[1(S)-(dicyclohexylphosphino)ethyl]-2(R)-(diphenylphosphino) ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino) ferrocene, 1-[1(R)-(diphenylphosphino)ethyl]-2(S)-(di-tert-butylphosphino)ferrocene, 1-[1(S)-(diphenylphosphino)

ethyl]-2(R)-(di-tert-butylphosphino)ferrocene, 1-{1(R)-[bis(3,5-dimethylphenyl)phosphino]ethyl}-2(S)-(diphenylphosphino)ferrocene, 1-{1(S)-[bis(3,5-dimethylphenyl)phosphino]ethyl}-2(R)-(diphenylphosphino)-ferrocene, 1-{1(R)-[bis(4-tert-butylphenyl)phosphino]ethyl}-2(S)-(diphenylphosphino)ferrocene, 1-{1(S)-[bis(4-tert-butylphenyl)phosphino]ethyl}-2(R)-(diphenylphosphino)ferrocene, 1-[1(S)-(9-phosphabicyclo[3.3.1]nonan-9-yl)ethyl]-2(R)-(diphenylphosphino)ferrocene and 1-[1(R)-(9-phosphabicyclo[3.3.1]nonan-9-yl)ethyl]-2(S)-(diphenylphosphino)ferrocene.

32. The process according to claim 31, wherein X is chlorine.

33. The process according to claim 32, wherein $R^1$ and $R^{1'}$ together form a cyclopentane-1,3-diyl group.

34. The process according to claim 33, wherein $R^2$ is an optionally substituted phenyl group.

35. The process according to claim 27, wherein the chiral bidentate diphosphine ligand is chosen from the group consisting of (R)-2,2'-bis(diphenylphosphino)-1,1'-binaphthalene, (S)-2,2'-bis(diphenylphosphino)-1,1'-binaphthalene, (R)-2,2'-bis(diphenylphosphino)-6,6'-dimethyl-1,1'-biphenyl, (S)-2,2'-bis(diphenylphosphino)-6,6'-dimethyl-1,1'-biphenyl, 1-[1(R)-(dicyclohexylphosphino)ethyl]-2(S)-(diphenylphosphino)ferrocene, 1-[1(S)-(dicyclohexylphosphino)ethyl]-2(R)-(diphenylphosphino)ferrocene, 1-[1(R)-(diphenylphosphino)ethyl]-2(S)-(diphenylphosphino)ferrocene, 1-[1(S)-(diphenylphosphino)ethyl]-2(R)-(diphenylphosphino)ferrocene, 1-[1(R)-(diphenylphosphino)ethyl]-2(S)-(di-tert-butylphosphino)ferrocene, 1-[1(S)-(diphenylphosphino)ethyl]-2(R)-(di-tert-butylphosphino)ferrocene, 1-{1(R)-[bis(3,5-dimethylphenyl)phosphino]ethyl}-2(S)-(diphenylphosphino)ferrocene, 1-{1(S)-[bis(3,5-dimethylphenyl)phosphino]ethyl}-2(R)-(diphenylphosphino)-ferrocene, 1-{1(R)-[bis(4-tert-butylphenyl)phosphino]ethyl}-2(S)-(diphenylphosphino)ferrocene, 1-{1(S)-[bis(4-tert-butylphenyl)phosphino]ethyl}-2(R)-(diphenylphosphino)ferrocene, 1-[1(S)-(9-phosphabicyclo[3.3.1]nonan-9-yl)ethyl]-2(R)-(diphenylphosphino)ferrocene and 1-[1(R)-(9-phosphabicyclo[3.3.1]nonan-9-yl)ethyl]-2(S)-(diphenylphosphino)ferrocene.

36. The process according to claim 27, wherein X is chlorine.

37. The process according to claim 27, wherein $R^1$ and $R^{1'}$ together form a cyclopentane-1,3-diyl group.

38. The process according to claim 27, wherein $R^2$ is an optionally substituted phenyl group.

* * * * *